United States Patent
Fan et al.

(10) Patent No.: US 10,760,961 B2
(45) Date of Patent: Sep. 1, 2020

(54) METHOD FOR TESTING RETINAL IMPLANT

(71) Applicant: IRIDIUM MEDICAL TECHNOLOGY CO., LTD., Hsinchu (TW)

(72) Inventors: Long-Sheng Fan, Hsinchu (TW); Hsin Chen, Hsinchu (TW); Yung-Chan Chen, Hsinchu (TW)

(73) Assignee: IRIDIUM MEDICAL TECHNOLOGY CO., LTD., Hsinchu (TW)

( * ) Notice: Subject to any disclaimer, the term of this patent is extended or adjusted under 35 U.S.C. 154(b) by 111 days.

(21) Appl. No.: 15/815,330

(22) Filed: Nov. 16, 2017

(65) Prior Publication Data

US 2018/0143071 A1    May 24, 2018

Related U.S. Application Data

(60) Provisional application No. 62/423,346, filed on Nov. 17, 2016.

(51) Int. Cl.
*G01J 1/44* (2006.01)
*A61F 2/14* (2006.01)
*G01J 1/18* (2006.01)
*G01J 1/08* (2006.01)
*G01J 1/02* (2006.01)

(52) U.S. Cl.
CPC .......... *G01J 1/44* (2013.01); *A61F 2/14* (2013.01); *G01J 1/0228* (2013.01); *G01J 1/08* (2013.01); *G01J 1/18* (2013.01); *G01J 2001/444* (2013.01)

(58) Field of Classification Search
CPC ... A61F 2/14; G01J 1/0228; G01J 1/08; G01J 1/18; G01J 1/44; G01J 2001/44
See application file for complete search history.

(56) References Cited

U.S. PATENT DOCUMENTS

| | | | |
|---|---|---|---|
| 4,090,132 A * | 5/1978 | Alexander | G01R 31/2637 324/762.01 |
| 9,155,881 B2 | 10/2015 | Fan | |
| 2003/0196921 A1* | 10/2003 | Giordano | A61B 50/30 206/370 |
| 2004/0098067 A1* | 5/2004 | Ohta | A61F 9/08 607/54 |

OTHER PUBLICATIONS

Wikipedia, Prosigns for Morse code, Nov. 11, 2009 (Year: 2009).*
Zhengnian et al., IEEE Transactions on Biomedical Engineering. vol. 42. No. 5. May 1995 (Year: 1995).*

* cited by examiner

*Primary Examiner* — Kyle R Quigley
(74) *Attorney, Agent, or Firm* — Muncy, Geissler, Olds & Lowe, P.C.

(57) ABSTRACT

The present invention relates to a method for testing a retinal implant. After an implantable device for interfacing with retinal cells is provided, an external stimulus is applied to the implantable device so that the implantable device transmits a first pulse to a processing device through a wireless interface. When a conversion unit is controlled to gradually decrease an output voltage until the implantable device outputs an output voltage lower than a reference voltage, the implantable device transmits a signal different from the first pulse to the processing device through the wireless interface. The processing device determines a current value of a pixel unit according to a time difference between the first pulse and the signal.

8 Claims, 7 Drawing Sheets

METHOD FOR TESTING RETINAL IMPLANT

FIELD OF THE INVENTION

The present invention relates to a testing method, and particularly to a method for self-testing and electrode activation of a retinal implant.

BACKGROUND OF THE INVENTION

Among current patients with visual deterioration, some patients choose to implant a retinal implant to improve vision. At present, the only retinal implant approved by the U.S. Food and Drug Administration (FDA) has only 60 pixels and is expensive; therefore, the improvement to the quality of life for patients is limited. In view of this, many companies and research institutes are actively devoted to the improvement of retinal implant microsystems. For example, a non-planar chipset is proposed in U.S. Patent Publication No. 9155881B2 filed by the applicant, which has a flexible structure formed by bending and deforming a planar shape. The flexible structure includes at least one layer of semiconductor material, and openings of a plurality of cut-out channels around a central portion of the flexible structure extend from a periphery of the flexible structure toward the central portion, and the plurality of cut-out channels are used for decreasing a displacement stress generated when the planar shape is bent and deformed into the flexible structure. Outside the flexible structure, the flexible structure is further joined to at least one fixing structure via a joining structure, so that the flexible structure maintains its bent state.

A retinal implant detects the intensity of light, and electrically detects the intensity of light with a high spatial resolution and stimulates healthy optic nerves, for example, bipolar cells in a retina. To avoid that a leakage current damages nerve tissue or causes a system damage, only a stimulation electrode of the retinal implant is exposed and in contact with the tissue, and the rest is hermetically sealed, not allowing a test point or an electrode to be exposed.

As a result, it is difficult to ensure that the manufactured retinal implant functions properly before transplantation. However, functional assurance is an essential element in reducing the risk and costs of retina transplantation.

In addition, there is also a need for a method for effectively reducing the impedance of an electrode to enhance a stimulation effect.

SUMMARY OF THE INVENTION

One objective of the present invention is to overcome the drawback of conventional testing methods for retinal implants, which have difficulties in testing functions of retinal implants before transplantation.

Another objective of the present invention is to reduce the electrode impedance of a retinal implant to facilitate the transfer of stimulation current(s) to nerve tissue(s).

To achieve the above objective, the present invention provides a system for testing a retinal implant, including an implantable device for interfacing with retinal cells, an amplification unit, and a processing device. The implantable device is disposed in a conductive medium, and includes at least one pixel unit and a conversion unit connected to the pixel unit. Each pixel unit includes a photoelectric sensor that receives illumination from a light source and outputs a current, and the conversion unit converts the current into a square wave voltage. The amplification unit is electrically connected to the implantable device via the conductive medium and obtains the square wave voltage to output an amplified square wave voltage. The processing device receives the amplified square wave voltage and determines the quality of the pixel unit according to a relationship between the amplified square wave voltage and the intensity of the light source.

In an embodiment of the present invention, the conversion unit includes a first amplifier, a first resistor, a chopping switch, and a digital-to-analog converter. The first resistor and the chopping switch are connected in parallel to an output end and a first input end of the first amplifier, and the digital-to-analog converter is connected to a second input end of the first amplifier.

In an embodiment of the present invention, the amplification unit includes a second amplifier, a first capacitor, a second capacitor, and a second resistor. The second capacitor and the second resistor are connected in parallel to an output end and an input end of the second amplifier, the first capacitor is connected in series to the input end of the second amplifier, and a non-inverting potential end of the second amplifier is connected to a ground end.

In an embodiment of the present invention, the processing device includes a data extractor.

The present invention provides a method for testing a retinal implant, including:

providing an implantable device for interfacing with retinal cells, where the implantable device includes at least one pixel unit and a conversion unit connected to the pixel unit, each pixel unit outputs a current in response to an external stimulus, and the conversion unit converts the current into an output voltage;

transmitting, by the implantable device, a first pulse to a processing device through a wireless interface;

decreasing, by the conversion unit, the output voltage gradually; and transmitting, by the implantable device, a signal different from the first pulse to the processing device through the wireless interface when the output voltage is lower than a reference voltage, and determining, by the processing device, the current value of the pixel unit according to a time difference between the first pulse and the signal.

In an embodiment of the present invention, the wireless interface is formed by a first wireless device or a second wireless device provided separately from the first wireless device.

In an embodiment of the present invention, the first wireless device and the second wireless device are a first induction coil and a second induction coil respectively.

In an embodiment of the present invention, the external stimulus is a light source.

In an embodiment of the present invention, the signal comprises at least two consecutive second pulses.

In an embodiment of the present invention, the implantable device is packaged in a sterilization bag.

In an embodiment of the present invention, the processing device includes a data extractor and a computer connected to the data extractor.

Another embodiment of the invention provides a system for testing a retinal implant, including an implantable device for interfacing with retinal cells, a first wireless device connected to the implantable device, a second wireless device provided separately from the first wireless device, and a processing device connected to the second wireless device. The implantable device includes at least one pixel unit, a conversion unit connected to the pixel unit, and a comparator connected to the conversion unit. Each pixel unit includes a photoelectric sensor that receives illumination from a light source and outputs a current, the conversion unit converts the current into an output voltage, and the comparator comprises a first input end for inputting a reference voltage and a second input end for inputting the output voltage of the conversion unit. The conversion unit gradually decreases the output voltage and returns a first pulse to the processing device. When the output voltage is lower than the reference voltage, the comparator outputs a high signal to cause the implantable device to return a second pulse different from the first pulse to the processing device. The processing device determines the quality of the pixel unit according to a relationship between a time difference between the first pulse and the second pulse and the intensity of the illuminating light.

In an embodiment of the present invention, the processing device includes a data extractor.

In an embodiment of the present invention, a method for testing a retinal implant is provided, including:

providing an implantable device for interfacing with retinal cells, where the implantable device is disposed in a conductive medium and includes at least one pixel unit and a conversion unit connected to the pixel unit, each pixel unit includes a photoelectric sensor that receives illumination from a light source and outputs a current, and the conversion unit converts the current into an output voltage;

receiving, by the pixel, from a light source and output a current;

decreasing gradually, by the conversion unit, the output voltage;

transmitting, by the implantable device, a first pulse to a processing device through a wireless interface; and transmitting, by the implantable device, a second pulse different from the first pulse to the processing device through the wireless interface when the output voltage is lower than a reference voltage, and determining, by the processing device, the quality of the pixel unit according to a relationship between a time difference between the first pulse and the second pulse and the intensity of the illuminating light.

In an embodiment of the present invention, the wireless interface is formed by a first wireless device and a second wireless device provided separately from the first wireless device.

In an embodiment of the present invention, a method for reducing the impedance of a retinal implant is further provided, including:

step 1: providing an implantable device for interfacing with retinal cells, where the implantable device includes at least one pixel unit, and each pixel unit includes a plurality of microelectrodes;

step 2: placing the implantable device in a conductive medium;

step 3: increasing a voltage across each of the plurality of microelectrodes from an initial voltage to a positive voltage at a first constant speed to form a positive voltage difference between the initial voltage and the positive voltage;

step 4: decreasing the voltage across each of the plurality of microelectrodes from the positive voltage to a negative voltage at a second constant speed to form a negative voltage difference between the initial voltage and the negative voltage; and repeating step 3 to step 4 N times.

In an embodiment of the present invention, an implantable device for interfacing with retinal cells is further provided. The implantable device includes: a plurality of pixel units, where the plurality of pixel units each includes a photoelectric sensor for receiving illumination from a light source and outputting a current; and a conversion unit connected to the pixel unit and capable of converting the current output from the pixel unit into a non-inverting potential end of an output voltage, wherein the pixel unit and the conversion unit are integrally disposed as a chip.

In an embodiment of the present invention, the conversion unit is a combination of a transimpedance amplifier and a unit-gain buffer amplifier.

In an embodiment of the present invention, the conversion unit includes a first amplifier, a first resistor, a chopping switch, and a digital-to-analog converter. The first resistor and the chopping switch are connected in parallel to an output end and a first input end of the first amplifier, and the digital-to-analog converter is connected to a second input end of the first amplifier.

In an embodiment of the present invention, a comparison unit is further included. The comparison unit includes a comparator and a voltage follower. The comparator has a first input end and a second input end connected to the output end of the first amplifier, the voltage follower comprises a non-inverting potential end connected to a reference voltage, a low potential end connected to form a feedback loop, an output end connected to form a feedback loop, and the second input end of the comparator is connected to the feedback loop.

In an embodiment of the present invention, a switching unit is further included. The switching unit is connected between the output end of the first amplifier of the conversion unit and the output end of the voltage follower, and the switching unit includes a first switch, a second switch, and a node provided between the first switch and the second switch.

Compared with the prior art, the present invention has the following advantages:

(1) According to the testing method of the present invention, the retinal implant can be self-tested before being actually transplanted so as to determine whether the retinal implant can function normally. In addition, the impedance of the retinal implant can also be reduced more than ten times, thereby achieving the effect of activating a pixel electrode thereof.

(2) The testing method of the present invention can be implemented by transmission of wireless signals, and estimation is performed based on a time interval between pulses. Therefore, compared with the conventional testing method, the present invention has the advantage of simple decoding.

(3) In the prior art, an analog-to-digital converter (ADC) needs to be used for an analog-to-digital conversion. However, the testing system of the present invention uses only a digital-to-analog converter (DAC) and a comparator to convert an analog signal amplitude into a time difference, not only saving more power, but also saving more space in the design of the retinal implant.

(4) The implantable device provided by the present invention can operate the activation method and the testing method for reducing the impedance without additionally using an analog-to-digital converter (ADC). In comparison, the invention has the advantages of reducing costs and simplifying complex circuits.

DETAILED DESCRIPTION OF THE PREFERRED EMBODIMENTS

Figure 1:
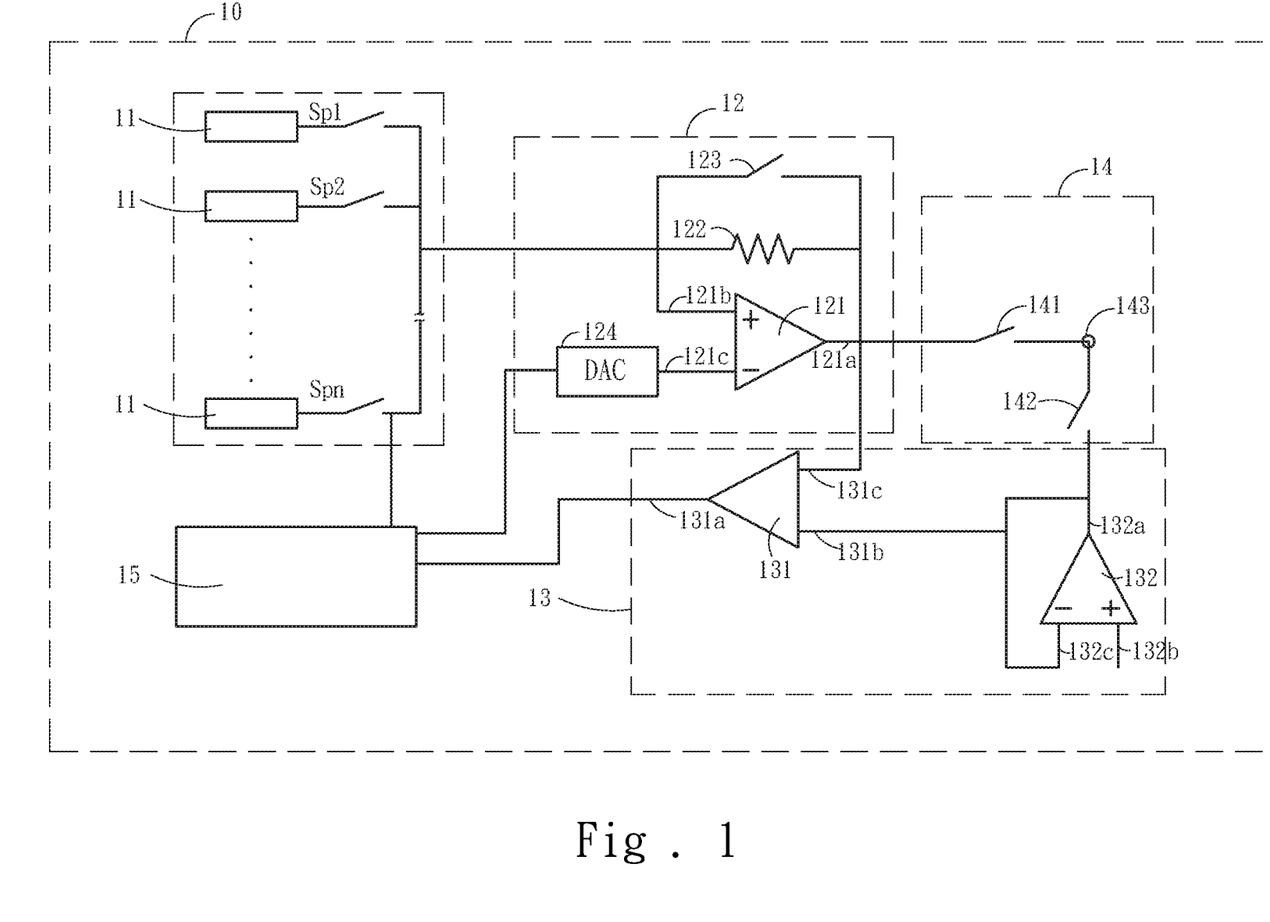
FIG. 1 is a schematic circuit diagram of an implantable device of the present invention.

The detailed description and the technical content of the present invention will now be described in conjunction with the drawings as follows:

FIG. 1 is a schematic diagram of an implantable device 10 of a system for testing a retinal implant of the present invention. The implantable device 10 mainly includes at least one pixel unit 11 and a conversion unit 12 connected to the pixel unit 11. In addition, in other embodiments, the implantable device 10 may further optionally include a comparison unit 13 and/or a switching unit 14, and a digital core 15 connected to the pixel unit 11, the conversion unit 12, and the comparison unit 13.

Each pixel unit 11 includes a photo sensor (not shown) and a controller Spi, where i is a positive integer between 1 and n. In an embodiment of the present invention, n is preferably between 3000 and 5000.

The conversion unit 12 includes a first amplifier 121, a first resistor 122, a chopping switch 123, and a digital-to-analog converter 124. The first resistor 122 and the chopping switch 123 are connected in parallel to an output end 121a and a first input end 121b of the first amplifier 121, and the digital-to-analog converter 124 is connected to a second input end 121c of the first amplifier 121.

In other embodiments, the implantable device 10 may further optionally include the comparison unit 13, the switching unit 14, and the digital core 15.

The comparison unit 13 includes a comparator 131 and a voltage follower 132. The comparator 131 has an output end 131a, a first input end 131b, and a second input end 131c connected to the output end 121a of the first amplifier 121. The voltage follower 132 has a non-inverting potential end 132b connected to a reference voltage ($V_{ref}$), an inverting potential end 132c connected to form a feedback loop, and an output end 132a connected to form a feedback loop. The first input end 131b of the comparator 131 is connected to the feedback loop. The switching unit 14 is connected between the output end 121a of the first amplifier 121 of the conversion unit 12 and the output end 132a of the voltage follower 132 of the comparison unit 13, and the switching unit 14 includes a first switch 141, a second switch 142, and a node 143 provided between the first switch 141 and the second switch 142.

The digital core 15 is connected to the pixel unit 11 and the conversion unit 12. In other embodiments including the comparison unit 13, the digital core 15 is further electrically connected to the comparison unit 13. The digital core 15 controls opening and closing of the pixel unit 11, the switching unit 14, and the chopping switch 123.

Next, a method of self-testing the retinal implant and activating a pixel electrode of the above-described implantable device 10 will be described. In the self-testing section, the following embodiments are described by using an example in which the implantable device 10 produces an electrical signal when receiving illumination from a light source. However, in other embodiments, the device and the method disclosed by the present invention are also applicable to receive electrical signals generated by other external stimuli.

Embodiment 1: Self-Testing Method

Figure 2A:
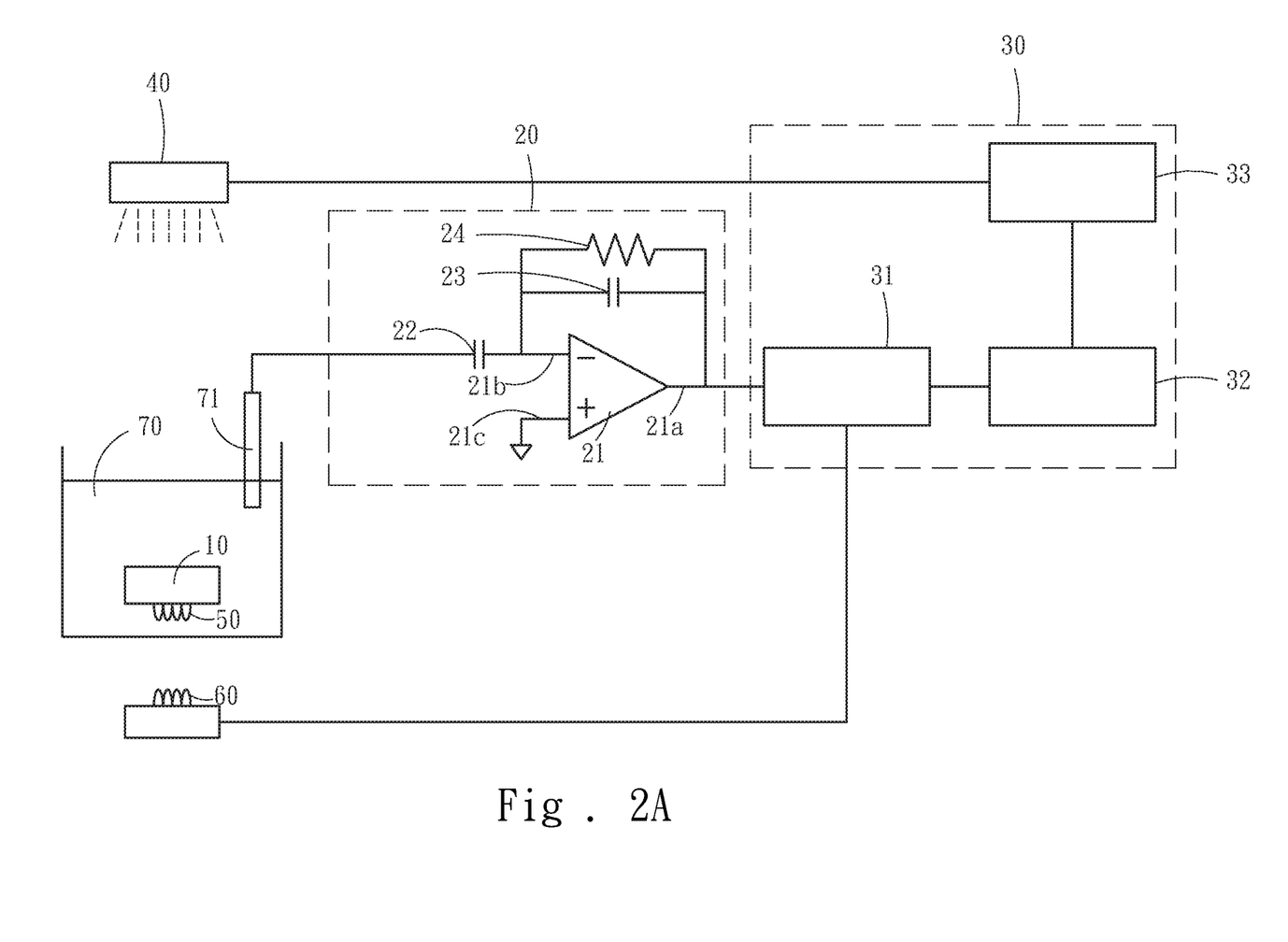
FIG. 2A is a schematic diagram of testing a retinal implant according to the Embodiment 1 of the present invention.
Figure 2B:
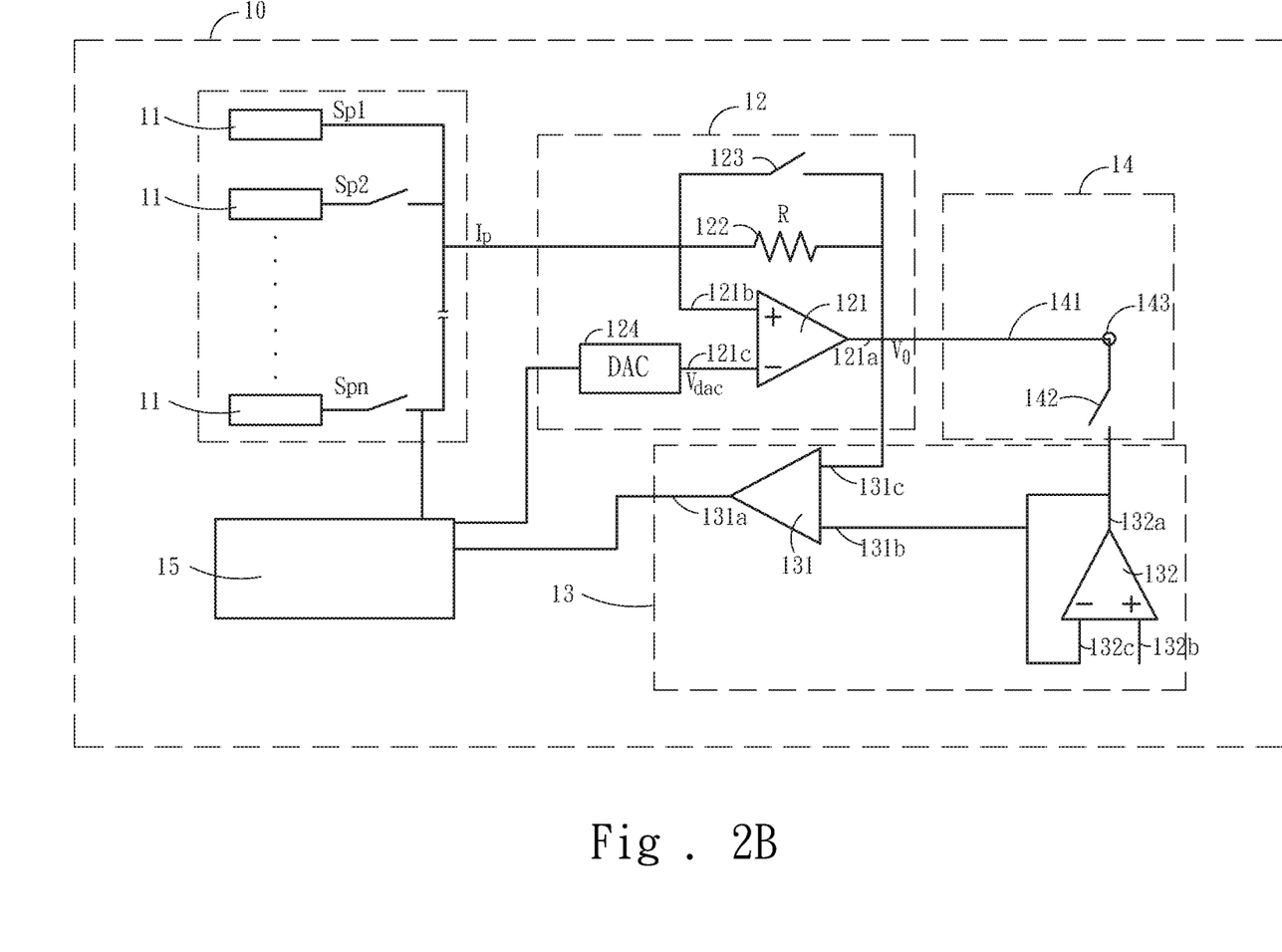
FIG. 2B is a schematic circuit diagram of the implantable device when the testing of the Embodiment 1 is performed.

FIG. 2A is a schematic diagram of testing a retinal implant according to the Embodiment 1 of the present invention; and FIG. 2B is a schematic circuit diagram of an implantable device 10 when the testing of the Embodiment 1 is performed.

FIG. 2A includes a system for testing a retinal implant. The system further includes an amplification unit 20 and a processing device 30 in addition to the implantable device 10 for interfacing with retinal cells described above. In this embodiment, the system further includes a first wireless device 50 connected to the implantable device 10 and a second wireless device 60 provided separately from the first wireless device 50. The first wireless device 50 and the second wireless device 60 form a wireless interface, and the first wireless device 50 and the second wireless device 60 use induction coils for transmitting signals and power in a radio frequency (RF) form.

The amplification unit 20 includes a second amplifier 21, a first capacitor 22, a second capacitor 23, and a second resistor 24. The second capacitor 23 and the second resistor 24 are connected in parallel to an output end 21a and an inverting potential end 21b of the second amplifier 21. The first capacitor 22 is connected in series to the inverting potential end 21b of the second amplifier 21, and a non-inverting potential end 21c of the second amplifier 21 is connected to a ground end.

The processing device 30 includes a data extractor 31, and may further optionally include a computer 32 and a controller 33. The computer 32 is electrically connected to the data extractor 31 and/or the controller 33 so as to control the data extractor 31 and/or the controller 33. The controller 33 may be connected to a light source 40 to control the intensity of the light source 40.

The testing method in Embodiment 1 is mainly carried out by the above testing system. The implantable device 10 is placed in a conductive medium 70, and the conductive medium 70 may be a buffer solution.

When operations of the testing method of this embodiment are performed using the implantable device 10 shown in FIG. 1, the first switch 141 of the switching unit 14 is "ON" and the second switch 142 is "OFF". A specific circuit configuration is shown in FIG. 2B. In each test, only one pixel unit 11 is selected for testing to read out a stimulated current of the single pixel unit 11. In this embodiment, Sp1 is taken as an example, and the chopping switch 123 periodically opens and closes through adjustment of the digital core 15 according to a square wave. When the chopping switch 123 in the conversion unit 12 is "OFF", the first amplifier 121 and the first resistor 122 in the conversion unit 12 function as a transimpedance amplifier. When the chopping switch 123 is "ON", the first amplifier 121 functions as a unit-gain buffer. In this case, $V_o$ output by the output end 121a of the first amplifier 121 is equal to a constant analog voltage $V_{dac}$ generated by the digital-to-analog converter 124.

Accordingly, the conversion unit 12 may convert an output current ($I_p$) of the pixel unit 11 into a square wave voltage $V_0$, and the square wave voltage $V_0$ is output from the output end 121*a* of the first amplifier 121, and $V_0$ is represented by the following Formula 1.

$$V_0 = V_{dac} - I_p \times R \quad \text{Formula 1}$$

That is, the pixel unit 11 to be tested receives illumination from a light source so that the photo sensor outputs the output current ($I_p$), and the output current ($I_p$) enters the conversion unit 12. When the chopping switch 123 is controlled by a square wave, the output current ($I_p$) of the pixel unit 11 is converted into a square wave voltage $V_0$ whose amplitude is linearly proportional to the current.

Referring again to FIG. 2A, the amplification unit 20 is electrically connected to the node 143 of the implantable device 10 via an electrode 71 and the conductive medium 70 and outputs an amplified square wave voltage in response to obtaining the square wave voltage $V_0$, and then the data extractor 31 of the processing device 30 receives the amplified square wave voltage and determines the quality of the pixel unit 11 according to a relationship between the amplified square wave voltage and the intensity of the light source. The processing device 30 may further optionally include the computer 32 and the controller 33, so that the computer 32 is electrically connected to the data extractor 31 and/or the controller 33 to control the data extractor 31 and/or the controller 33. For example, the computer 32 controls the implantable device 10 via the data extractor 31, the first wireless device 50, and the second wireless device 60 to connect another pixel unit 11 to the output end 121*a* of the first amplifier 121, and the computer 32 may also control the light source 40 to emit light to be received by a pixel unit 11 to be tested and the above testing method is repeated.

The above "determining the quality of the pixel unit 11" refers to determining the quality by obtaining a corresponding amplified square wave voltage according to the intensity of a light source and comparing the amplified square wave voltage with a theoretical value.

Embodiment 2: Self-Testing Method

Figure 3A:
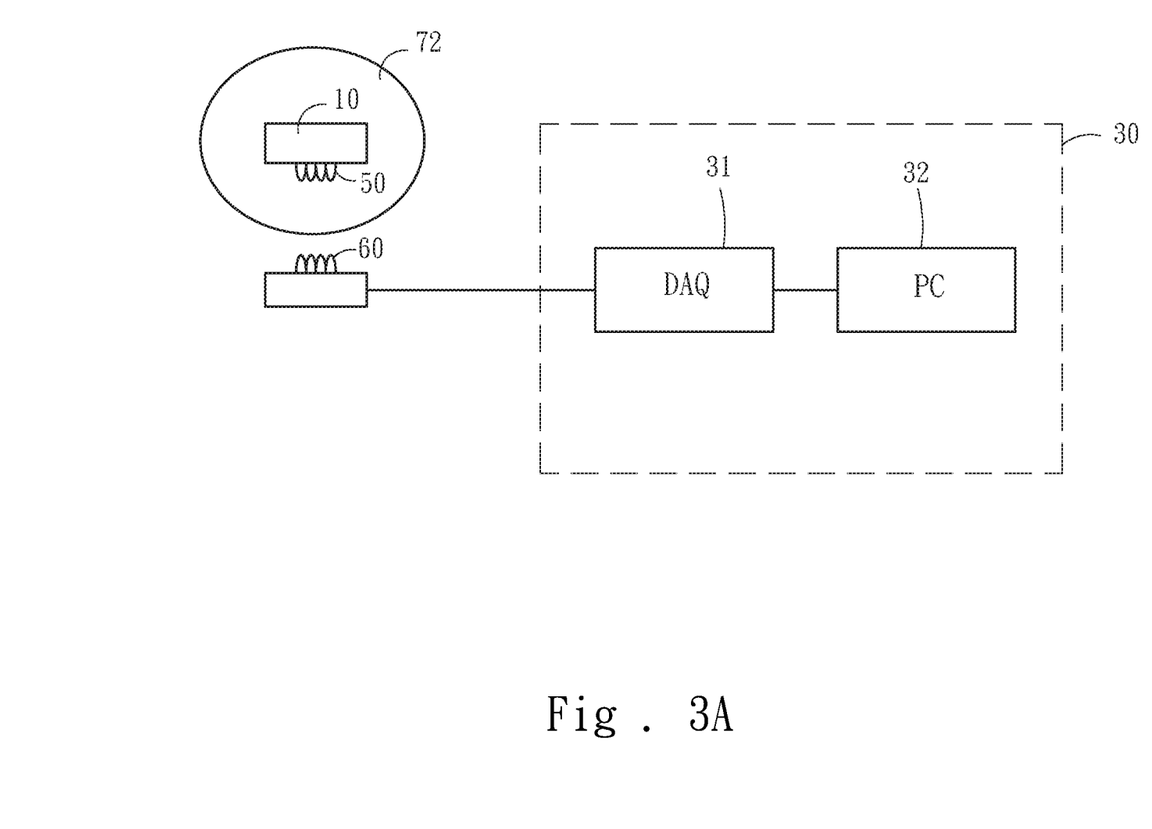
FIG. 3A is a schematic diagram of testing the retinal implant according to the Embodiment 2 of the present invention.

The Embodiment 2 of the present invention is mainly performed via transmission of wireless signals and power. For example, when the implantable device 10 is sterilized and sealed in a sterilization bag 72, the implantable device 10 may be tested by using the following method. However, this is merely an example for description. In other embodiments, the implantable device 10 may be tested in a wireless manner by using the method of this embodiment in another state, for example, after encapsulation but before packaging.

Figure 3B:
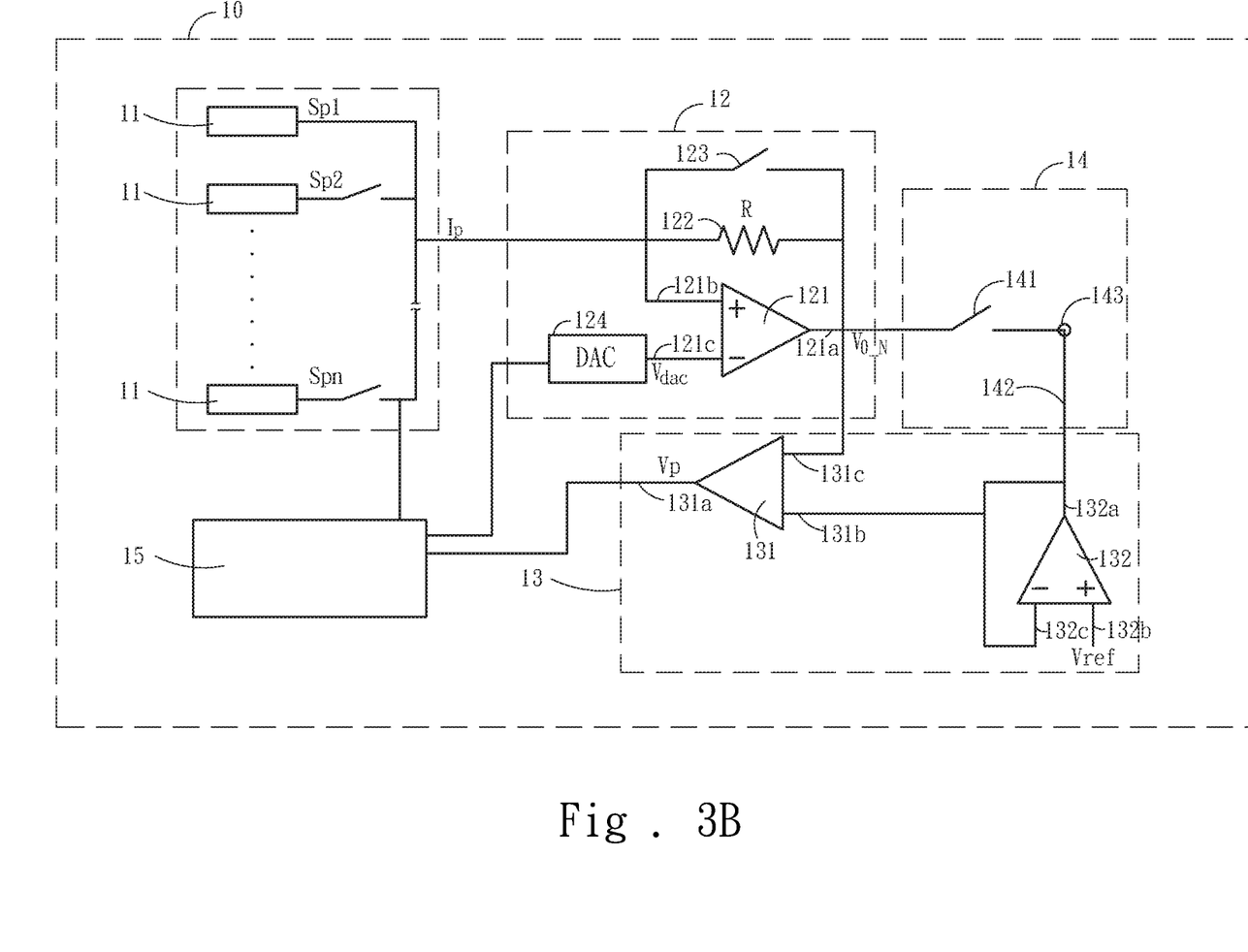
FIG. 3B is a schematic circuit diagram of the implantable device when the testing of the Embodiment 2 is performed.
Figure 3C:
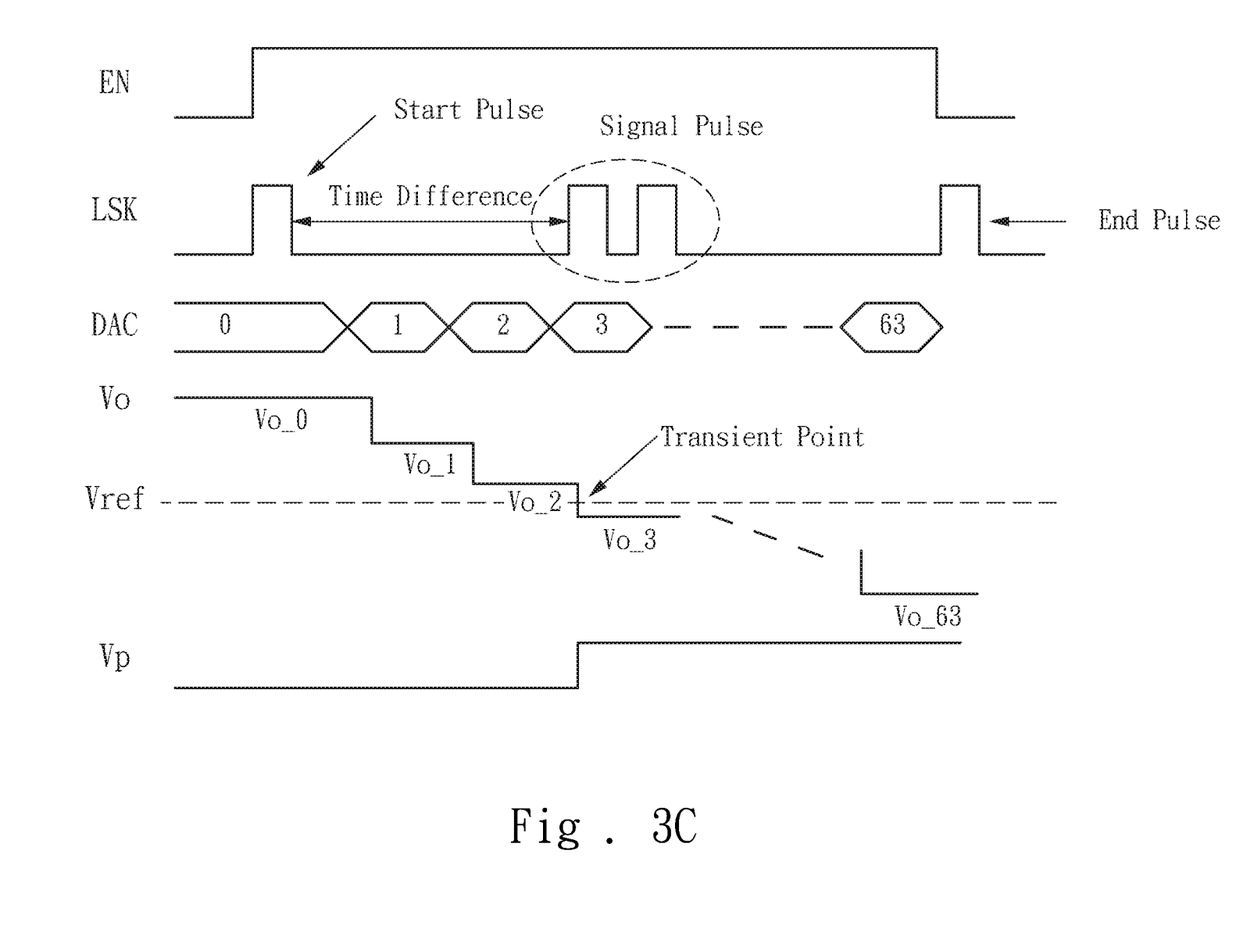
FIG. 3C is a schematic diagram of pulse signals for performing the Embodiment 2.

Refer to FIG. 3A, FIG. 3B, and FIG. 3C, which are respectively a schematic diagram of testing a retinal implant according to the Embodiment 2 of the present invention, a schematic circuit diagram of an implantable device 10 when the testing of the Embodiment 2 is performed, and a schematic diagram of pulse signals for performing the Embodiment 2.

In this method, in addition to aforementioned implantable device 10 for interfacing with retinal cells and the processing device 30, further provided a first wireless device 50 connected to the implantable device 10 and a second wireless device 60 provided separately from the first wireless device 50. In this embodiment, the first wireless device 50 and the second wireless device 60 form a wireless interface, and the first wireless device 50 and the second wireless device 60 use induction coils and transmit signals in an RF form.

When operations of the testing method of this embodiment are performed using the implantable device 10 shown in FIG. 1, both the chopping switch 123 in the conversion unit 12 and the first switch 141 of the switching unit 14 are "OFF", and the second switch 142 of the switching unit 14 is "ON", so that the first amplifier 121 and the first resistor 122 function as a transimpedance amplifier. A specific circuit configuration is shown in FIG. 3B. When the pixel unit 11 receives illumination from a light source, the photoelectric sensor of the pixel unit 11 outputs an output current ($I_p$), and the output current ($I_p$) enters the conversion unit 12. The output end 121*a* of the first amplifier 121 outputs an output voltage $V_{0\_N}$, and the digital-to-analog converter 124 outputs a voltage $V_{dac}$.

The voltage of $V_{dac}$ is represented by the following Formula 2:

$$V_{dac} = V_{dac0} - N \times V_{delta} \quad \text{Formula 2}$$

$V_{dac0}$ represents a voltage when the digital-to-analog (DAC) resolution value of the digital-to-analog converter 124 is zero, $V_{delta}$ is the resolution of digital-to-analog (DAC), and N is the value of the digital-to-analog resolution. Therefore, the output voltage $V_{0\_N}$ is represented by the following Formula 3:

$$V_{0\_N} = V_{dac0} - N \times V_{delta} - I_p \times R \quad \text{Formula 3}$$

Refer again to FIG. 3C. During testing, the system enters a testing mode. The pixel unit 11 receives illumination from the light source and outputs the output current ($I_p$) via the photoelectric sensor of the pixel unit 11, and the output current ($I_p$) enters the conversion unit 12. At this moment, after the digital core 15 issues a trigger signal EN (enable), the implantable device 10 returns a start pulse to the processing device 30 as a header signal in a load shift keying (LSK) manner via the induction coil. Next, by increasing the resolution value of the digital-to-analog converter 124 at a constant speed, the digital-to-analog converter 124 is caused to begin to decrease its output voltage ($V_{dac}$), so that the conversion unit 12 also gradually decreases the output voltage $V_0$. The start pulse is defined as a first pulse. This embodiment uses LSK as an example. In other embodiments, however, phase shift keying (PSK), amplitude-shift keying (ASK), or other equivalent manners may be used as well.

When $V_0$ drops to $V_{ref}$, the output voltage ($V_p$) of the comparator 131 changes from low to high. At this time, the implantable device 10 returns a single pulse to the processing device 30 via the induction coil in the load shift keying manner, where the signal pulse is a signal different from the start pulse, and in this embodiment, the signal pulse is a combination of two identical or different consecutive pulses. When the resolution value of the digital-to-analog converter 124 is equal to 63, the trigger signal EN changes from high to low, so that the implantable device 10 generates an end pulse and transmits the end pulse to the processing device 30, indicating that reading of data of the pixel unit 11 is completed. In addition, the resolution value may be set to several tens to several thousands as needed without being limited to 63 in this embodiment.

In this embodiment, the comparator 131 compares the output voltage $V_0$ with a reference voltage ($V_{ref}$) set by the voltage follower 132. When the output voltage $V_0$ is lower than the reference voltage ($V_{ref}$), the implantable device 10 transmits the second pulse different from the first pulse to the processing device 30 through the wireless interface. A time difference between the first pulse and the second pulses is inversely proportional to the output current of the pixel unit 11 to be tested. Therefore, the processing device 30 may determine the quality of the pixel unit 11 according to a relationship between the time difference between the first pulse and the second pulse and the intensity of the illuminating light.

The above "determining the quality of the pixel unit 11" refers to determining the quality by obtaining a corresponding time difference according to the intensity of the light source and comparing the time difference with a theoretical value.

After the pixel unit 11 is read by using the foregoing wirelessly transmitted pulse, the processing device 30 may control the implantable device 10 via, for example, the computer 32, to connect another pixel unit 11 to the output end 121a of the first amplifier 121 to repeat the above steps.

Embodiment 3: Electrode Activation Method

The "electrode activation" in the present invention refers to reducing an impedance between an electrode and a liquid by using a cyclic voltammetry method in the electrochemistry field to facilitate the transfer of a stimulated current to nerve tissue.

Figure 4:
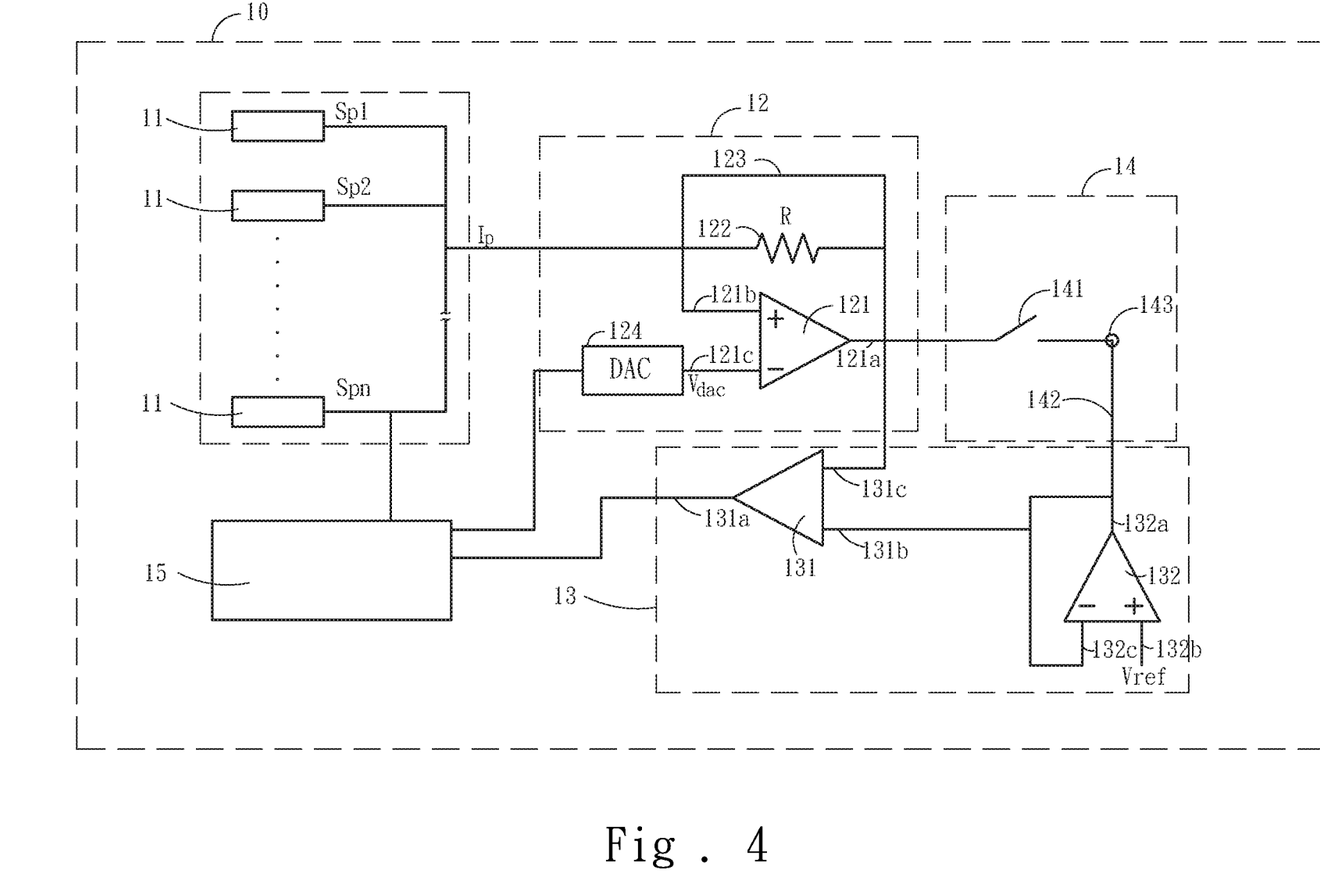
FIG. 4 is a schematic circuit diagram of the implantable device when an electrode activation method of the Embodiment 3 is performed.

In the embodiment, the electrode activation method is performed within a conductive medium 70, and has the following steps.

First of all, the processing device 30 transmits a command signal to the digital core 15 of the implantable device 10 through the first wireless device 50 and the second wireless device 60.

Next, the digital core 15 transmits a controlling signal to the digital-to-analog converter 124. The controlling signal instructs the digital-to-analog converter 124 to increase or decrease the voltage of the second input end 121c. That is, for each time when the controlling signal is transmitted, an output voltage of the digital-to-analog converter 124, the $V_{delta}$ of the Formula 2, will be increased or decreased accordingly.

Therefore, as the voltage of the digital-to-analog converter 124 starts to change, a voltage of the electrode within the pixel unit 11 will be identical to the voltage of the digital-to-analog converter 124. At the same time, a voltage of the node 143 will be $V_{ref}$ so that a voltage difference between the electrode of the pixel unit 11 and the node 143 will be obtained, thereby activating the electrode within the pixel unit 11.

As for the issues regarding the range of the increasing or the decreasing, and the speed to perform the electrode activation method, both of these issues are depending on the frequency of the processing device 30 to transmit the command signal and/or the time interval between two command signals. However, the frequency and the time interval mentioned above can be set or adjusted based on the needs.

The electrode activation step of the present invention facilitates electrochemical reaction between the electrode of the pixel unit 11 and the liquid. The whole steps are simple, and after the above steps are repeated several times, the impedance between the electrode of the pixel unit 11 and the liquid will decrease, which facilitates the transfer of a stimulated current to neurons by implantable device 10.

When the operations of the testing method of this embodiment are performed using the implantable device 10 shown in FIG. 1, the first switch 141 of the switching unit 14 of the implantable device 10 is "OFF", the second switch 142 is "ON", and the chopping switch 123 in the conversion unit 12 is "ON". A specific circuit configuration is shown in FIG. 4. As can be seen from FIG. 4, the conversion unit 12 functions as a unit-gain buffer and forces potentials of all pixel units 11 to be the same as $V_{dac}$. On the other hand, with setting of the voltage follower 132, a voltage output from the output end 132a to the node 143 will be the same as the reference voltage ($V_{ref}$) input to the non-inverting potential end 132b. The specific method is as follows.

Step 1: Providing the implantable device 10 for interfacing with retinal cells, where the implantable device 10 includes at least one pixel unit 11, and each pixel unit 11 includes a plurality of microelectrodes. The pixel unit 11 in the implantable device 10 each includes a photoelectric sensor and a microelectrode. In an embodiment, the pixel unit 11 further includes a sensing element (such as a light sensing element, an electrical sensing element, or other applicable sensing elements), a processor, and/or a driving circuit.

Step 2: The implantable device 10 is placed in a conductive medium 70, the applicable conductive medium 70 of the embodiment may be a buffer solution.

Step 3: A voltage across the microelectrode is increased from an initial voltage to a positive voltage at a first constant speed (for example, +100 mV/s) to form a positive voltage difference between the initial voltage and the positive voltage (for example, +0.8V). In this embodiment, the initial voltage is the reference voltage ($V_{ref}$), and by using the circuit configuration described above, $V_{dac}$ is gradually increased to increase the potential of the pixel unit 11 until the positive voltage is reached.

Step 4: Subsequently, the voltage across the microelectrode is decreased from the positive voltage to a negative voltage at a second constant speed (for example, −100 mV/s) in a manner similar to that in step 3, to form a negative voltage difference (for example, −0.6 V) between the initial voltage and the negative voltage.

The above step 3 and step 4 are repeated N times. N is a positive integer, for example, from 2 times to 1000 times, from 2 times to 500 times, or from 2 times to 200 times, though the present invention is not limited thereto. In addition, considering power consumption, only a part of pixels may be activated during the activation. For example, if it is assumed that the implantable device 10 has 4000 pixels, only 50 to 150 pixels may be activated at a time. However, the electrode activation method will be performed several times on each implantable device 10 until all pixels included therein, for example, 4000 pixels, are all being activated. That is, in the embodiment, all microelectrodes inside the pixels of the implantable device 10 will be activated.

This architecture allows the chip to be immersed in the buffer solution to reduce the impedance between the electrode within the pixel unit 11 of the implantable device 10 and the liquid by using the cyclic voltammetry method, thereby achieving the effect of activating its pixel electrode, so that a better signal effect is achieved when the implantable device 10 is actually implanted into a human body for operation.

What is claimed is:

1. A method for testing a retinal implant, comprising:
   providing an implantable device for interfacing with retinal cells, wherein the implantable device comprises at least one pixel unit and a conversion unit connected to the at least one pixel unit;
   providing an external stimulus for the at least one pixel unit to respond and output a current, the current being converted into an output voltage by the conversion unit;
   transmitting, by the implantable device, a first pulse to a processing device through a wireless interface;

adjusting, by the conversion unit, a square wave to make a chopping switch of the conversion unit performed periodically on and off;

decreasing, by the conversion unit, the output voltage gradually;

transmitting, by the implantable device, a signal, which is different from the first pulse, to the processing device through the wireless interface when the output voltage is lower than a reference voltage; and acquiring, by the processing device, a current value of the pixel unit according to a time difference between the first pulse and the signal which are acquired from the implantable device.

2. The method for testing a retinal implant of claim 1, wherein the wireless interface is formed by a first wireless device or a second wireless device provided separately from the first wireless device.

3. The method for testing a retinal implant of claim 2, wherein the first wireless device and the second wireless device are a first induction coil and a second induction coil respectively.

4. The method for testing a retinal implant of claim 1, wherein the external stimulus is a light source.

5. The method for testing a retinal implant of claim 1, wherein the signal is at least two consecutive second pulses which are identical.

6. The method for testing a retinal implant of claim 1, wherein the implantable device is packaged in a sterilization bag.

7. The method for testing a retinal implant of claim 1, wherein the processing device comprises a data extractor and a computer connected to the data extractor.

8. The method for testing a retinal implant of claim 1, wherein the signal is at least two consecutive second pulses which are different.

* * * * *